United States Patent [19]

Salce et al.

[11] 3,941,801

[45] Mar. 2, 1976

[54] PROCESS FOR PREPARING SUBSTITUTED NITROIMIDAZOLES

[75] Inventors: Ludwig Salce, Brewster, N.Y.; Erwin F. Schoenewaldt, Watchung, N.J.

[73] Assignee: Merck & Co., Inc., Rahway, N.J.

[22] Filed: Dec. 5, 1974

[21] Appl. No.: 529,864

Related U.S. Application Data

[63] Continuation of Ser. No. 286,638, Sept. 6, 1972, abandoned, Continuation-in-part of Ser. No. 40,449, May 25, 1970, abandoned.

[52] U.S. Cl. ............... 260/309; 204/158 R; 260/997
[51] Int. Cl.$^2$ ...................................... C07D 233/94
[58] Field of Search .................. 260/309; 204/158 R

[56] References Cited
OTHER PUBLICATIONS

Beringer et al. J. Org. Chem. 1967, Vol. 32, pp. 2630–2632.

Meerwein et al. Liebigs Ann. Chem. 1060, Vol. 632, pp. 38–55.

*Primary Examiner*—Natalie Trousof
*Attorney, Agent, or Firm*—Richard A. Thompson; J. Jerome Behan

[57] ABSTRACT

2-(p-Fluorophenyl)-1-alkyl or 1-(2'-hydroxyalkyl)-5-nitroimidazoles are prepared by reacting a dialkoxycarbonium salt, or a 1,3-dioxolenium salt, respectively, with 2-(p-fluorophenyl)-1-alkoxymethyl-4-nitroimidazole. The compounds prepared are useful in the control of enterohepatitis in poultry, especially in turkeys.

3 Claims, No Drawings

PROCESS FOR PREPARING SUBSTITUTED NITROIMIDAZOLES

RELATED CASES

This application is a continuation of U.S. Ser. No. 286,638, filed Sept. 6, 1972, now abandoned, which in turn is a continuation-in-part of U.S. Ser. No. 40,449, filed May 25, 1970, now abandoned.

This invention relates to new and novel processes for preparing 2-(p-fluorophenyl)-1-alkyl-5-nitroimidazole and 2-(p-fluorophenyl)-1-(2'-hydroxyethyl)-5-nitroimidazole. Both processes employ the same starting material, 2-(p-fluorophenyl)-1-alkoxymethyl-4(5)-nitroimidazole:

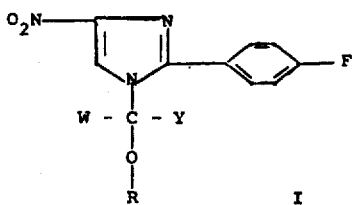

wherein Y and W are each hydrogen, loweralkyl, phenyl, or benzyl; and R is loweralkyl, phenyl, benzyl, loweralkanoyl, benzoyl, or loweralkenyl. Preferably, the starting compound is one in which W and Y are both hydrogen, and R is loweralkyl. More preferably, R is methyl. The most preferred starting material of this invention is 1-methoxymethyl-2-(p-fluorophenyl)4(5)-nitroimidazole.

The compounds (I) described above are claimed in co-pending application, U.S. Ser. No. 40,447, filed May 25, 1970 assigned to the same assignee. These compounds can be prepared using the following process; this process also being claimed and disclosed in the co-pending application:

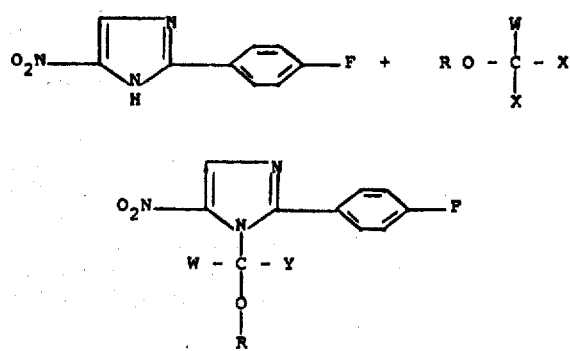

wherein X is halo, and can be bromo, fluoro, chloro, or iodo, and is preferably chloro. The other substitutents listed in the above equation are the same as above. Preferably, R is loweralkyl, and W and Y are hydrogen.

The starting material in this reaction is (p-fluorophenyl)-4(5)-nitroimidazole. This compound is generally known and described in the art. The reactant compound is a halomethyl ether or a halomethyl ester. The term "halogen" is used to mean chloro, bromo, fluoro, or iodo. Although halomethyl esters can be used in the above reaction, for instance, where R is loweralkanoyl or benzoyl, the preferred choice of reagent is a halomethyl ether when R is loweralkyl, phenyl, benzyl, or loweralkenyl. The most preferable halomethyl ether can be described as ROCH₂X wherein R is a loweralkyl group having 1-6 carbon atoms and X is a halogen which can be chloro, bromo, fluoro, or iodo, and is preferably chloro.

The 4(5)-nitroimidazole can be reacted with the chosen halomethyl ether with or without a solvent. If a solvent is used, one that is inert toward the reactant is preferably employed. Suitable solvents include benzene, dimethoxyethane, tetrahydrofuran, dioxane, methylene chloride, ether, ethyl acetate, hexane, or toluene. If the solvent is not employed, a sufficient excess of the halomethyl ether is used as the reaction medium. The two reactants in the optional solvent are mixed and then refluxed or heated to initiate the reaction. The preferred temperature is between 80°-110°C.

The reaction can also take place with or without an added base. The base is preferably one such as sodium methoxide, triethylamine, pyridine, or the like. If a base is used, it is employed in at least an equivalent amount, up to about 3 molar excess, based on the amount of halomethyl ether employed.

The reactants are mixed and allowed to react for a time which can vary between 15 minutes to 24 hours. The exact duration of the reaction is not critical, and it is preferred to continue the reaction until the product concentration reaches a maximum. The point at which the optimum product level is reached depends on the particular parameters of each experiment and can easily be determined by monitoring the example reaction.

The reaction is usually run at atmospheric pressure, although lower or higher pressures can be used if desirable for the particular reaction conditions.

The nitroimidazole and the halomethyl ether are usually employed in proportions so that the halomethyl ether is present in excess, generally from 1½ to 5 excess for maximum yield.

The above discussion discloses the preparation of the starting materials for this invention. It is, however, an object of this invention to use these starting materials in further processes to yield useful nitroimidazoles. These further processes constitute the inventive contribution of this disclosure.

The first process (Process A) of this invention yields as its product:

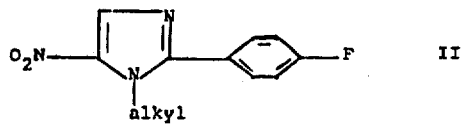

Preferably, the alkyl group is a loweralkyl group, having 1-6 carbon atoms. More preferably, the 1-methyl-2-(p-fluorophenyl)-5-nitroimidazole is the final product.

The reagent used to prepare the above nitroimidazole II is a dialkoxy-carbonium fluoroborate, or a dialkoxy-carbonium hexachloro (or fluoro) antimonate, which can be represented by the following formula:

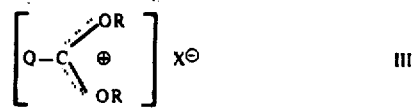

wherein R is loweralkyl having 1–6 carbon atoms, preferably methyl, X⁻ is BF₄, SbCl₆⁻, or SbF₆⁻, and Q is either H or OR, R having the same meaning as above, but Q is preferably H.

In addition to the dialkoxy-carbonium and trialkoxy-carbonium salts described above, other similar reagents can be used in this process. For instance, trimethyl- or triethyl-oxonium fluoroborate, (*Organic Syntheses*, Vol. 46, p. 120-121 and 113-115, respectively); or trimethyloxonium 2,4,6-trinitrobenzene sulfonate, (*Organic Syntheses*, Vol. 46, p. 122-126) can be prepared following the reference procedures. These reagents can then be employed in the instant inventive process.

The second process (Process B) of this invention yields as its product:

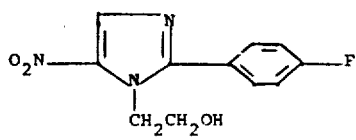   IV

This product is 1-(2'-hydroxyethyl)-2-(p-fluorophenyl)-5-nitroimidazole.

The reagent used in Process B is a 1,3-dioxolenium salt of the formula:

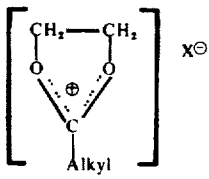   V wherein X⁻ is BF₄ or SbCl₆⁻, or SbF₆⁻, and alkyl has 1–6 carbon atoms.

The preparation and description of both reagents used in the processes of this invention is in *Liebigs. Ann.*, Vol. 632, pp. 38-55 (1960). The salts can be prepared following the general instructions, isolated, and then added to the starting material I. The salts can also be prepared in situ.

The preparation of the dialkoxy-carbonium salts can be generally described as follows: approximately 3 moles of a trialkyl orthoformate and 4 moles of boron trifluoride etherate, 6 moles of antimony pentachloride or 6 moles of antimony pentafluoride are mixed to yield approximately 3 moles of the dialkoxy-carbonium salt. After aging, (4–12 hours if the salt is to be isolated, under 1 hour if the salt is to be used in situ), the product can either be crystallized by gradual cooling at low temperature or used in further reactions. Preferably trimethyl orthoformate and BF₃ in a diethylether solution is used.

The 1,3-dioxolenium salts can be prepared by mixing boron trifuloride, antimony pentachloride, or antimony pentafluoride with 2-alkoxy-2-alkyl-1,3-dioxolane or 1-acetoxy-2-alkoxyethane, the alkoxy group in both cases having 1–6 carbon atoms, and preferably being ethoxy. The alkyl group also has 1–6 carbon atoms and preferably is methyl or ethyl. The molar ratio of the inorganic salt to the organic compound is approximately 4-6:3. The 1,3-dioxolenium salts are prepared by mixing the reagents and aging and isolating or using in situ in the further reaction.

The reaction conditions for both Process A and Process B of this invention are as follows. Both processes employ a solvent in the reaction. The solvent is preferably a solvent for all the reactants and products and does not participate in undesirable side reactions. Any solvent which may be used in these processes which does not have any protons bonded on oxygen or nitrogen, which would be susceptible to alkylation or hydroxyalkylation by the reagents employed. Suitable solvents include 1,2-dimethoxyethane, 1,2-dichloroethane, dioxane, methylene chloride, ethyl acetate, methyl formate, or 1,2-diacetoxy ethane.

The reactants are generally combined such that for each mole of imidazole employed, from 1 to 5 moles of the alkylation of hydroxyalkylation reagent is used. The reactants are initially combined in the chosen solvent at a temperature of from −10° to 30°C. and the reaction is raised to from about 30°C to the reflux temperature of the reaction mixture. The reaction mixture is maintained in this temperature range for from 15 minutes to 24 hours, with higher temperatures requiring shorter reaction times. During this period a solid precipitate generally forms, this solid being a quaternary intermediate compound. The exact structure of this intermediate quaternary compound depends on which Process, A or B, was used. However, Intermediates A and B can be treated by any of three different techniques, yielding in each case the same end product. The end product is the 1-alkyl-2-(p-fluorophenyl)-5-nitroimidazole in the case of Process A and 1-(2'-acyloxyethyl)-2-(p-fluorophenyl)-5-nitroimidazole in the case of Process B. The acyl moiety of the latter compound can be easily removed by hydrolysis to yield the final product, 1-(2'-hydroxyethyl)-2-(p-fluorophenyl)-5-nitroimidazole.

The three different treatments of the intermediate quaternary compounds are: (1) treatment with a nucleophile. A nucleophile as used in this specification and claims is defined as a polar reagent which provides a pair of unbonded electrons for the new bond at the 1-position of the product compound during a nucleophilic displacement reaction. Suitable nucleophiles include potassium iodide, potassium thiocyanate, hydrogen bromide, potassium cyanide, triethylamine, pyridine, or the like.

The nucleophilic displacement reaction between the quaternary salt and the nucleophiles takes place in a solvent at a temperature of from 20°C. to the reflux temperature of the reaction medium. The solvent may be any of the solvents employed in the preparation of the quaternary intermediate and in addition may include solvents previously excluded. Since the nucleophilic displacement reaction does not attack solvents with protons on oxygen or nitrogen the previous exclusion of those solvents is no longer necessary. Solvents as water, lower alkanols, or amines may be employed. It is preferred to employ a polar solvent for this step as the quaternary intermediates will be more soluble therein however this is only a matter of convenience as reaction will occur in a solvent in which the quaternary intermediate is sparingly soluble, although the reaction will proceed at a slower rate. The nucleophile reacts with the quaternary intermediates in a 1:1 molar ratio, however, it is convenient to employ the nucleophile in an excess as this renders the reaction somewhat more facile. Where a solvent is employed up to a 10 molar excess is generally sufficient. However, often it is convenient to employ the nucleophile itself as the solvent as in the cases of triethylamine, or pyridine. In such cases the excess moles are not calculated and generally sufficient nucleophile is employed as will make the reaction mixture mobile. The amount of nucleophile to be employed in any particular case may be readily determined by one skilled in this art. The product initially obtained from the reaction mixture is the acyl derivative of a desired 2-hydroxyethyl compound. The acyl group is readily removed with acid or basic hydrolysis. Under conditions in which hydronium ions are also present in the reaction system, e.g., when HBr is used., the system also acts as a hydrolyzing medium and the 1-(2'-hydroxyethyl)-2-(p-fluorophenyl)-5-nitroimidazole is produced directly from its respective acyl derivative.

The second treatment of the quaternary salt is a photolysis reaction using UV light irradiation of the quaternary salt in which said quaternary salt is in a quartz vessel. Where a suspending agent or a solvent is employed, it can be any of the usual UV transparent media, such as acetone, hexane, methanol, trifluoroacetic acid or the like. Additional UV transparent media will be readily ascertained by one skilled in this art. It has also been found that the irradiation does not need a solvent or suspending agent at all. The solid quaternary intermediate can be placed in an area of UV irradiation and agitated or spread on a thin film or by other techniques may be successfully irradiated. There are no temperature requirements for the irradiation as the reaction caused by the high energy irradiation is not dependent on the temperature of the reaction mixture. As the duration of the reaction may vary greatly depending upon the source of the irradiation the completion of the reaction is usually determined analytically by examining aliquot portions of the reaction mixture by gas or thin layer chromatography.

The third treatment of the quaternary is pyrolysis by heating the quaternary either alone, in a high boiling solvent, or suspending agent or in a lower boiling solvent or suspending agent under pressure, at a temperature of from 100°–300°C. The reaction is generally complete in from ¼ to 5 hours. The solvent is not a necessary requirement of this reaction. All that is necessary is that the quaternary intermediate be brought to the desired temperature range, irrespective as to whether the quaternary is in solution, suspension or alone. Where a solvent is desired for convenience there may be employed xylene, diglyme, or p-cymene.

The preferred treatment of all of the three above is the reaction with the nucleophile from the standpoint of both ease of application and yield of product. The preferred nucleophile treatment is with HBr, pyridine, or triethylamine.

The compounds prepared in the processes of this invention are useful in the control of trichomoniasis, amebiasis, or turkey enterohepatitis. For the latter purpose they may be administered to turkeys mixed with an element of turkey sustenance, e.g., feed or drinking water. Good control of enterohepatitis is obtained when 1-methyl or 1-(2'-hydroxyethyl)-2-(p-fluorophenyl)-5-nitroimidazole is incorporated in a turkey feed ration at a level from about 0.003% to about 0.1% by weight and preferably from about 0.006% to 0.05% by weight of the feed. The optimum concentration will depend to a large extent on the age of the bird, severity of the infection, and the particular compound employed. With the above feed levels, good control of the disease is obtained with no or minimal side effects or growth retardation of the turkeys.

The following examples illustrate the invention:

EXAMPLE 1

1-Methoxymethyl-2-(p-fluorophenyl)-4-nitroimidazole

To a stirred suspension of 2-(p-fluorophenyl)-4(5)-nitroimidazole (24.86 g., 0.120 mole) in 248 ml. of toluene is rapidly added 12.2 g (16.8 ml., 0.120 mole) of triethylamine. After stirring at 25° for 15 minutes, 10.2 g. (9.75 ml., 0.12 mole) of chloromethyl methyl ether is added dropwise over a 25 minute period maintaining the temperature between 25°–30°C.

The reaction mixture is then stirred for 3 hours. An additional 6.09 g. (8.4 ml., 0.060 mole) of triethylamine is added over a 1 minute period. A one degree temperature rise is noted. After stirring for 15 minutes, 5.1 g. (4.9 ml., 0.060 mole) of chloromethyl methyl ether is added dropwise over 15 minutes. A temperature rise of 4° is noted. The mixture is stirred for 1 hour at room temperature.

The reaction is then refluxed for one hour to improve the yield of the reaction. The reaction mixture is then diluted with 200 ml. of methylene chloride and washed with 2.5N HCL, 7.5 N $NH_4OH$ and 100 ml. of $H_2O$. Drying over $Na_2SO_4$ is followed by concentration to approximately 50 ml. Then 200 ml. of n-hexane is slowly added to the stirred reaction sludge and the mixture aged for 15 minutes. The precipitate is filtered, washed with 40 ml. of n-hexane and dried to afford 29.5 g. (0.117 mole, 97.4%) of 1-methoxymethyl-2-(p-fluorophenyl)-4-nitroimidazole as a tan powder: m.p. 113°–115°C.; λmax (0.1NHCl in $CH_3OH$): 305 nm (A% 276), 230 (520). Anal. for $C_{11}H_{10}FN_3O_3$.

Calcd: C, 52.59; H, 4.01; N, 16.73; Eq. Wt. 251.2.
Found: C, 52.63; H, 4.19; N, 16.95; Eq. Wt. 250.7.

EXAMPLE 2

2-Methyl-1,3-dioxolenium fluoroborate

A solution of triethyl orthoacetate (43.3 g., 2.67 moles), ethylene glycol (.65 g., 2.67 moles) and concentrated sulfuric acid (0.34 g.) is heated in an apparatus equipped for distillation and 214 g. (4.65 moles) of ethanol (bp 76–79°/1 atm. pot temp 86°–100°C.) is collected. The reaction solution is cooled to 40°C. and 8.6 g. of potassium carbonate is added. Reinitiation of the distillation afforded a second fraction of 57.3 g. (bp 78°–144°C., pot temp 102°–147°C.) consisting of 70% of ethanol and 30% of III. The third fraction (bp 144°–145°C., pot temp (148°–180°C.) yielded 268 g. (2.02 mole, 76%) of 2-ethoxy-2-methyl-1,3-dioxolane as a colorless liquid which was 99+% pure by vpc.

To a vigorously stirred solution of 14.5 g. (0.110 mole) of 2-ethoxy-2-methyl-1,3-dioxolane in 27.5 ml. of dry methylene chloride (KF 0.02 mg/ml) at 5°C under a nitrogen atmosphere is added dropwise 20.8 g. (0.146 mole) of freshly distilled boron trifluoride etherate over a 30 minute period. The reaction temperature is maintained between 5°–10°C. The reaction mixture is stirred for an additional hour at 5°–10°C.).

The dioxolenium fluoroborate can be isolated at this point of filtration and washing with 3 × 15 ml. of methylene chloride. These operations are conducted under a nitrogen atmosphere. The product is dried at 25°C./vac and affords 17.4 g. (0.100 mole, 90%) of 2-methyl-1,3-dioxolenium fluoroborate as a white powder.

Using a similar process, the 2-ethyl-1,3-dioxolenium hexachloroantimonate salt, 2-propyl-1,3-dioxolenium hexafluoro antimonate salt, 2-methyl-1,3-dioxolenium hexafluoro antimonate salt, and the 2-methyl-1,3-dioxolenium hexachloro antimonate salt can be prepared using 2-ethoxy-2-ethyl-1,3-dioxolane with $BF_3$, 2-ethoxy-2-n-propyl-1,3-dioxolane with $SbCl_5$, 2-ethoxy-2-methyl-1,3-dioxolane with $SbF_5$, and 2-ethoxy-2-methyl-1,3-dioxolane with $SbCl_5$, respectively.

When it is not desired to isolate the fluoroborate reagent, the mother liquor is removed with the aid of a filter stick and then the salt is washed with dry methylene chloride, with 15 minute stirring periods during each wash. Methylene chloride (55 ml.) is then added in preparation for the next step of the process.

EXAMPLE 3

1-(2'-Hydroxyethyl)-2-(p-fluorophenyl)-5-nitroimidazole

To the slurry of the dioxolenium salt from Example 2 is added a solution of 1-methoxymethyl-2-(p-fluorophenyl)-4-nitroimidazole, 12.56 g. in 65 ml. of dry methylene chloride. The resulting mixture is refluxed for 16 hours with vigorous agitation. A precipitate forms during reflux, resulting in a sludge. To this sludge is added 50 ml. of 2N HBr; the methylene chloride is distilled off. The resulting solution is refluxed for 3½ hours, cooled to 0°C. and adjusted to pH 10 with 61 ml. of 5N NaOH, maintaining vigorous stirring and a temperature of 0°-10°C. during the pH adjustment. After aging for 1 hour at 10°C.,) the precipitated crude product is filtered off, washed with $H_2O$ and dried at 64°C./vac.

The crude product (15.0 g. of methanol-insoluble inorganic salts are removed at this point) and the filter cake are washed with 10 ml. of hot methanol. To the combined hot filtrates is added 12 ml. of concentrated $NH_4OH$ followed by the slow addition of 50 ml. of water maintaining a temperature of 60°C., cooling overnight, filtration of the crystalline solid, washing with water, and drying at 64°C/vac., yielded 9.9 g. (0.035 mole, 79.2%) of the product, 1-(2'-hydroxyethyl)-2-(p-fluorophenyl)-5-nitroimidazole, as yellow needles, m.p. 164.5°-166.5°C.

The product 1-(2'-hydroxyethyl)-2-(p-fluorophenyl)-5-nitroimidazole is also prepared in good yield when other previously prepared 1,3-dioxolenium salts are used. For instance, when 2-n-propyl-1,3-dioxolenium hexachloro antimonate, 2-ethyl-1,3-dioxolenium fluoroborate, or 2-methyl-1,3-dioxolenium hexafluoro antimonate salts are used in the above procedure, the desired product is prepared.

The above procedure describes the use of a nucleophile, HBr, to yield the final desired product from the quaternary intermediate compound. The other procedures are as follows:

To the sludge formed after the first step of this reaction is added 50 ml. of a 10% solution of KI in acetone, and the reaction process continued as described. The product, 1-(2'-acetoxyethyl)-2-(p-fluorophenyl)-5-nitroimidazole is isolated and identified in good yield. This product can be hydrolyzed in 99+% yield to the desired 1-(2'-hydroxyethyl)-2-(p-fluorophenyl)-5-nitroimidazole.

100 Ml. of pyridine can also be added to the sludge. After refluxing for two hours, the product 1-(2'-acetoxyethyl)-2-(p-fluorophenyl)-5-nitroimidazole is isolated.

The sludge can also be suspended in a solvent having a high boiling point and heated. For instance, 1 gm. of the crude material prepared in the first step of this example is dissolved in actone and passed through a gas chromatograph at 250°C. A peak is noted which has the same retention time as the 1-(2'-acetoxyethyl)-2-(p-fluorophenyl)-5-nitroimidazole. The material can be collected after pyrolysis and identified. After hydrolysis, the product, 1-(2'-hydroxyethyl)-2-(p-fluorophenyl)-5-nitroimidazole is recovered in good yield.

The quaternary material can also be dissolved in a solvent such as methanol and treated with UV irradiation, using a Hanovia UV lamp treatment for one-half hour. After treatment, the material is recrystallized and found to yield the 1-(2'-acetoxyethyl)-2-(p-fluorophenyl)-5-nitroimidazole in good quantities.

EXAMPLE 4

1-Methyl-2-(p-fluorophenyl)-5-nitroimidazole

1-Methoxymethyl-2-(p-fluorophenyl)-4-nitroimidazole (6.28 g.) is placed into a 100 ml. 3-neck round bottom flask equipped with a stirrer, thermometer, addition funnel, and a gas inlet and outlet tube. Then 15 ml. of methyl formate and 10.9 ml. of trimethyl orthoformate is added. The flask is flushed with nitrogen and the contents were cooled, with stirring, to 0°-5°C. Then 12.6 ml. of boron trifluoride ethereate is added to the addition funnel. The $BF_3$ etherate is added dropwise to the reaction mixture while maintaining the temperature below 5°C. After the addition was complete (within 15 minutes), the clear solution was aged at 0°-5°C. for 10 minutes. The ice bath is then removed and the solution stirred at room temperature under a nitrogen atmosphere. After 1 hour, a solid precipitates. This mixture is stirred at room temperature for 18 hours. Then 25 ml. of methyl formate was added and the mixture stirred in an ice bath for 15 minutes. The product is collected by filtration, washed with methyl formate and dried at 60°C. A crude yield of 7.12 g. of 1-methoxymethyl-2-(p-fluorophenyl)-3-methyl-4-nitroimidazolium fluoroborate, the quaternary intermediate compound, melting at 164° -166°C., is obtained.

One g. of the above imidazolium fluoroborate is dissolved in acetone. The solution is injected into a gas chromatograph at 250°C. The recovered fraction is identified as 1-methyl-2-(p-fluorophenyl)-5-nitroimidazole, m.p. 166°-168°C.

The above discussion involves the use of the reagent, dimethoxy-carbonium fluoroborate prepared in situ. The reagent dimethoxy-carbonium hexachloro antimonate can also be used to prepare the 1-methyl-2-(p-fluorophenyl)-5-nitroimidazole product.

The quaternary intermediate compound can also be refluxed with 2 N HBr, 2 N KI, 2N KSCN, or pyridine following the general procedure described in Example 3 to yield the final product, 1-methyl-2-(p-fluorophenyl)-5-nitroimidazole.

What is claimed is:

1. A process for preparing 1-(2'-hydroxyethyl)-2-(p-fluorophenyl)-5-nitroimidazole by reacting in a solvent selected from the group consisting of 1,2-dimethoxyethane, 1,2-dichloroethane, dioxane, methylene chloride, ethyl acetate, methyl formate or 1,2-diacetoxyethane at a temperature of from −10°C. to the reflux temperature of said solvent for from 15 minutes to 24 hours, each molar equivalent of a compound of the formula

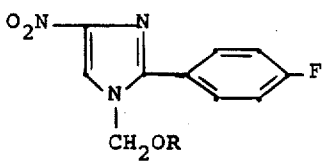

with from 1 to 5 molar equivalents of a compound of the formula:

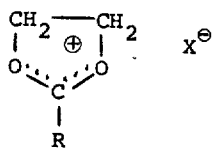

wherein X⁻ is BF₄⁻, SbCl₆⁻, or SbF₆⁻, and R is alkyl of 1–6 carbon atoms thereby forming a quaternary first intermediate; treating said quaternary first intermediate with ultraviolet irradiation thereby giving a second intermediate of the formula:

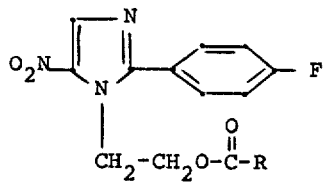

where R is as previously defined; and hydrolyzing the second intermediate.

2. A process for preparing 1-(2'-hydroxyethyl)-2-(p-fluorophenyl)-5-nitroimidazole by reacting in a solvent selected from the group consisting of 1,2-dimethoxyethane, 1,2-dichloroethane, dioxane, methylene chloride, ethyl acetate, methyl formate of 1,2-diacetoxyethane at a temperature of −10°C. to the reflux temperature of said solvent for from 15 minutes to 24 hours, 45 each molar equivalent of a compound of the formula:

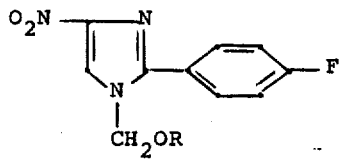

with from 1 to 5 molar equivalents of a compound of the formula:

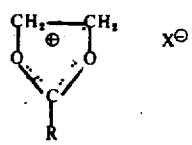

wherein X⁻ is BF₄⁻, SbCl₆⁻, and R is alkyl of 1–6 carbon atoms, thereby forming a quaternary first intermediate; heating said quaternary first intermediate at a temperature of from 100°C. to 300°C. for from ½ to 5 hours thereby forming a second intermediate of the formula:

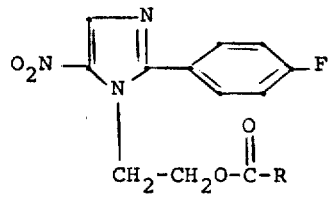

where R is as previously defined; and hydrolyzing the second intermediate.

3. A process of preparing 1-(2'-hydroxyethyl)-2-(p-fluorophenyl)-5-nitroimidazole by reacting in a solvent selected from the group consisting of 1,2-dimethoxyethane, 1,2-dichloroethane, dioxane, methylene chloride, ethyl acetate, methyl formate or 1,2-diacetoxyethane at a temperature of from −10°C. to the reflux temperature of said solvent for from 15 minutes to 24 hours a 1-loweralkoxymethyl-2-(p-fluorophenyl)-4-nitroimidazole with a 1,3-dioxolenium salt of the formula:

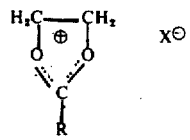

thereby forming a quaternary intermediate wherein:
X⁻ is BF₄⁻, SbCl₆⁻ or SbF₆⁻ and R represents an alkyl group of 1–6 carbon atoms; treating said quaternary intermediate with a polar nucleophile selected from the group consisting of potassium iodide, hydrogen bromide, potassium thiocyanate, potassium cyanide, triethylamine or pyridine; thereby forming a second intermediate:

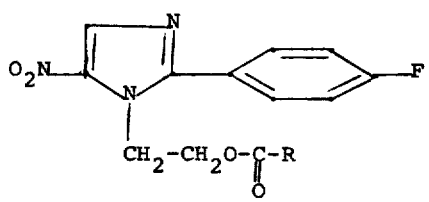

wherein R is as previously defined; and hydrolyzing the second intermediate.

* * * * *